United States Patent
Hamada et al.

(10) Patent No.: US 7,589,221 B2
(45) Date of Patent: Sep. 15, 2009

(54) PROCESS FOR PRODUCING (2R)-2-PROPYLOCTANOIC ACID AND INTERMEDIATE THEREFOR

(75) Inventors: Yasumasa Hamada, Chiba (JP); Tomoyuki Hasegawa, Sakai-gun (JP); Toshiaki Matsui, Sakai-gun (JP); Eiji Kasamatsu, Sakai-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 582 days.

(21) Appl. No.: 10/560,176

(22) PCT Filed: Jun. 9, 2004

(86) PCT No.: PCT/JP2004/008387

§ 371 (c)(1),
(2), (4) Date: Dec. 9, 2005

(87) PCT Pub. No.: WO2004/110972

PCT Pub. Date: Dec. 23, 2004

(65) Prior Publication Data

US 2006/0135802 A1    Jun. 22, 2006

(30) Foreign Application Priority Data

Jun. 10, 2003    (JP) .............................. 2003-164485

(51) Int. Cl.
*C07B 53/00* (2006.01)
*C07C 231/00* (2006.01)
*C07C 227/00* (2006.01)

(52) U.S. Cl. .......................... 554/114; 564/130; 562/606

(58) Field of Classification Search ........................ None
See application file for complete search history.

(56) References Cited

U.S. PATENT DOCUMENTS

| 3,864,387 | A | * | 2/1975 | Nelson ......................... 562/467 |
| 2003/0083231 | A1 | * | 5/2003 | Ahlem et al. .................. 514/2 |
| 2003/0096802 | A1 | * | 5/2003 | Ohuchida et al. ...... 514/210.17 |

FOREIGN PATENT DOCUMENTS

| JP | 1-275541 A | | 11/1989 |
| JP | 01-275541 A | * | 11/1989 |
| JP | 7-316092 A | | 12/1995 |
| WO | WO 99/58513 A1 | | 11/1999 |

OTHER PUBLICATIONS

Solomons, Organic Chemistry, 5th Edition, 1992, pp. 240-242.*

* cited by examiner

*Primary Examiner*—Paul A Zucker
(74) *Attorney, Agent, or Firm*—Sughrue Mion, PLLC

(57) ABSTRACT

The present invention relates to a process for producing (2R)-2-propyloctanoic acid, which comprises subjecting (2R)-2-hexyloxirane to a two-carbon adding reaction with ring-opening reaction, followed by a protecting reaction of a hydroxyl group to convert it to a compound represented by formula (I):

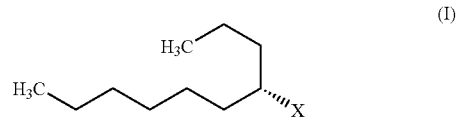

(I)

(wherein X represents an optionally protected hydroxyl group) and then subjecting the compound to a one-carbon adding reaction to convert it to (2R)-2-propyloctanamide, followed by recrystallization and hydrolysis. According to the process of the present invention, (2R)-2-propyloctanoic acid can be produced by less steps as compared with the conventional method without a dangerous reaction.

3 Claims, No Drawings

PROCESS FOR PRODUCING (2R)-2-PROPYLOCTANOIC ACID AND INTERMEDIATE THEREFOR

TECHNICAL FIELD

The present invention relates to a process for producing (2R)-2-propyloctanoic acid which is useful as a preventive and treating agent for neurodegenerative diseases caused by dysfunction of astrocytes, to an intermediate for its production, and to a method for purifying the same.

BACKGROUND ART

Racemic 2-propyloctanoic acid is known as a preventive and treating agent for neurodegenerative diseases caused by dysfunction of astrocytes (cf., for example, WO 99/58513). As a result of studies thereafter, it has been clarified that 2-propyloctanoic acid of an R-form has a particularly strong activity and, therefore, various investigations have been carried out for a process for an efficient production of an R-form substance.

With regard to a process for producing (2R)-2-propyloctanoic acid, (1) a process in which camphor sultam is used as an asymmetric auxiliary group, (2) a process in which L-prolinol is used as an asymmetric auxiliary group, (3) a process in which racemic 2-(2-propynyl)-octanoic acid is reduced after optical resolution (cf EP-A-1078921, JP-A-8-295648 and JP-A-8-291106), etc. are known.

With regard to a synthetic method for an optically active 4-alkanol which is one of the intermediates used for the production of (2R)-2-propyloctanoic acid, a process in which an optically active alkyloxirane is allowed to react with ethyl magnesium halide is disclosed (cf JP-A-1-275541).

DISCLOSURE OF THE INVENTION

In the conventional process for producing intermediates for the manufacture of (2R)-2-propyloctanoic acid, there are many steps and a dangerous reaction is accompanied therewith and, therefore, it is hardly said to be an efficient process for an industrial production of a medicament which is the final product.

Accordingly, an object of the present invention is to provide a production process which is suitable for an industrial production by which (2R)-2-propyloctanoic acid can be efficiently produced in less steps as compared with conventional processes and without a dangerous reaction.

As a result of intensive investigations, the present inventors have succeeded in the production of (2R)-2-propyloctanoic acid having a high optical purity (99% ee or more) in three steps from (2R)-2-hexyloxirane via (2R)-2-proyloctanamide having good crystallinity and excellent purifying property and thus the present invention has been completed.

Also, (2R)-2-propyloctanamide, (1S)-1-propylheptyl p-toluenesulfonate and (1S)-1-propylheptyl 4-methanesulfonate which are intermediates useful in the process for producing (2R)-2-propyloctanoic acid according to the present invention are novel compounds.

Thus, the present invention relates to the followings.

1. A process for producing (2R)-2-propyloctanoic acid, which comprises:
subjecting (2R)-2-hexyloxirane to a two-carbon adding reaction with ring-opening reaction, followed by a protecting reaction of a hydroxyl group to convert it to a compound represented by formula (I):

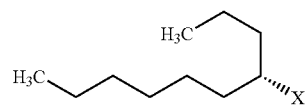

wherein X represents a hydroxyl group which may be protected, and then
subjecting the compound to a one-carbon adding reaction to convert it to (2R)-2-propyloctanamide, followed by recrystallization and hydrolysis.

2. A process for producing (2R)-2-propyloctanoic acid, which comprises hydrolyzing (2R)-2-propyloctanamide.
3. A process for producing (2R)-2-propyloctanamide, which comprises subjecting a compound represented by formula (I):

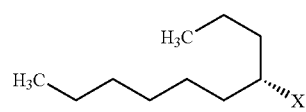

wherein X represents the same meaning as in the above 1, to a one-carbon adding reaction.
4. (2R)-2-Propyloctanamide.
5. Substantially pure (2R)-2-propyloctanamide.
6. A compound represented by formula (I):

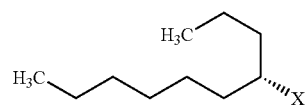

wherein X represents an optionally protected hydroxyl group.
7. The compound according to the above 6, wherein X is p-toluenesulfonyloxy or methanesulfonyloxy.
8. A process for producing (2S)-2-propyloctanoic acid, which comprises hydrolyzing (2S)-2-propyloctanamide.
9. A process for producing (2S)-2-propyloctanamide, which comprises subjecting a compound represented by the formula (II):

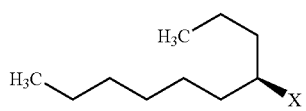

wherein X represents an optionally protected hydroxyl group,
to a one-carbon adding reaction.
10. A process for producing (2S)-2-propyloctanoic acid, which comprises:
subjecting (2S)-2-hexyloxirane to a two-carbon adding reaction with ring-opening reaction, followed by a protective reaction of a hydroxyl group to convert it to a compound represented by the formula (II), and then subjecting the compound to a one-carbon adding reaction to convert it to (2S)-2-propyloctanamide, followed by recrystallization and hydrolysis.

11. (2S)-2-Propyloctanamide.
11. Substantially pure (2S)-propyloctanamide.
13. A compound represented by the formula (II):

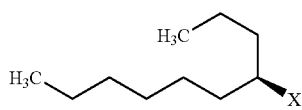

wherein X represents an optionally protected hydroxyl group.

14. The compound according to the above 13, wherein X is p-toluenesulfonyloxy or methanesulfonyloxy.
15. A process for producing them, and the like.

In the present specification, the "high purity" means that both chemical purity and optical purity are high.

In the present specification, the "substantially pure" means that the chemical purity is 95% or more and the optical purity is 95% ee or more.

The "optionally protected hydroxyl group" represented by X in the compound of formula (I) used in the production process of the present invention means a "hydroxyl group which is protected by a removable protective group". Examples of the "hydroxyl group which is protected by a removable protective group" include methanesulfonyloxy, p-toluenesulfonyoxy, chloromethanesulfonyloxy, trichloromethanesulfonyloxy, trifluoromethanesulfonyloxy, dimethylphosphonoxy, diethylphosphonoxy, trifluoromethyloxy, benzenesulfonyloxy, naphthalenesulfonyloxy, p-bromobenzenesulfonyloxy, p-nitrobenzenesulfonyloxy, m-nitrobenzenesulfonyloxy, o-nitrobenzensulfonyloxy and the like. Preferred are methanesulfonyloxy, p-toluenesulfonyloxy, chloromethanesulfonyloxy, trichloromethanesulfonyloxy, trifluoromethanesulfonyloxy and benzenesulfonyloxy; and more preferred are methanesulfonyloxy and p-toluenesulfonyloxy.

The process of the present invention is carried out according to the following reaction steps (A) to (C). The step (A) is a conversion reaction in which (2R)-2-hexyloxirane is subjected to a two-carbon adding reaction with ring-opening reaction, followed by a protective reaction of a hydroxyl group to convert it to a compound represented by formula (I); the step (B) is a conversion reaction in which the compound represented by formula (I) is subjected to a one-carbon adding reaction, followed by hydrolysis to convert it to (2R)-2-proyloctanamide; and the step (C) is a reaction in which (2R)-2-propyloctanamide is hydrolyzed to obtain (2R)-2-propyloctanoic acid.

Reaction scheme

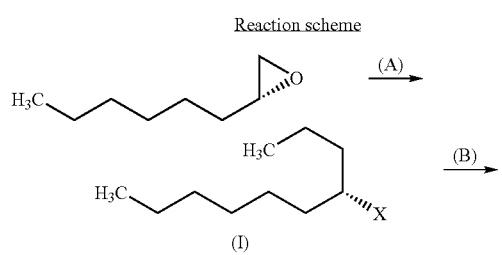

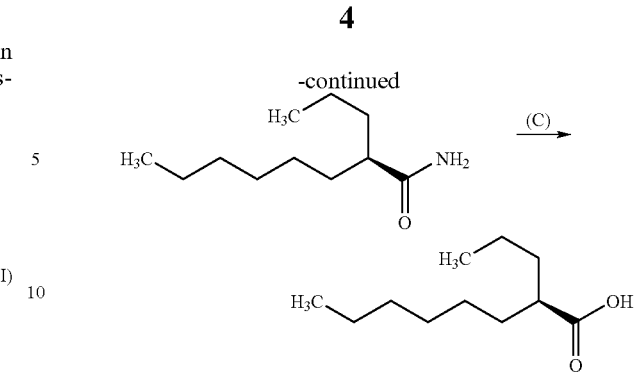

Hereinafter, each of the steps is explained below in detail.

Step (A):

The conversion reaction of (2R)-2-hexyloxirane to a compound represented by formula (I) is carried out by subjecting (2R)-2-hexyloxirane to a two-carbon adding reaction with ring-opening reaction, followed by a protective reaction of a hydroxyl group.

The two-carbon adding reaction with ring-opening reaction is known and is carried out, for example, by reacting (2R)-2-hexyloxirane with an organic metal reagent having an ethyl group (e.g., ethyl magnesium chloride, ethyl magnesium bromide, diethyl magnesium, ethyl lithium, ethyl aluminum dichloride, diethyl aluminum chloride, triethyl aluminum, ethyl trimethyl silane, triethyl manganese lithium, ethyl zinc chloride, diethyl zinc, tetraethyl tin, triethyl tin chloride, triethyl tin bromide, diethyl tin dichloride, diethyl tin dibromide, ethyl tin trichloride, triethyl borane, a reagent wherein they are mixed with the following metal catalyst in any ratio, etc.) at −78 to 20° C. in an organic solvent (e.g., tetrahydrofuran, 2-methyltetrahydrofuran, 1,4-dioxane, diethyl ether, cyclopentyl methyl ether, 2-methoxy ethyl ether, benzene, toluene, dimethoxyethane, hexane, heptane, cyclohexane, dichloromethane, chloroform, dichloroethane, hexamethyl phosphoramide, dimethylimidazolidinone, N,N-dimethylformamide, N,N-dimethylacetamide, N-methylpyrrolidone, dimethyl sulfoxide, 1,3-dimethyl-3,4,5,6-tetrahydro-2-pyrimidinone, a mixed solvent of two or more thereof in any ratio, etc.) in the presence or absence of a metal catalyst (e.g., copper cyanide, copper chloride, copper iodide, copper bromide, lithium chloride, boron trifluoride. diethyl ether complex, titanium chloride, etc.).

The protective reaction of a hydroxyl group is known and it is carried out, for example, at −78 to 50° C. by adding a sulfonyl chloride (e.g., methanesulfonyl chloride, p-toluenesulfonyl chloride, chloromethanesulfonyl chloride, trichloromethanesulfonyl chloride, trifluoromethanesulfonyl chloride, benzenesulfonyl chloride, naphthalenesulfonyl chloride, p-bromobenzenesulfonyl chloride, p-nitrobenzenesulfonyl chloride, m-nitrobenzenesulfonyl chloride, o-nitrobenzenesulfonyl chloride, etc.), a phosphoryl chloride (e.g., diphenylphosphoryl chloride, diethylphosphoryl chloride, etc.) or an acid anhydride (e.g., trifluoroacetic acid, anhydride, etc.), using an organic solvent (e.g., tetrahydrofuran, 2-methyltetrahydrofuran, 1,4-dioxane, diethyl ether, cyclopentyl methyl ether, 2-methoxy ethyl ether, benzene, toluene, dimethoxyethane, hexane, heptane, cyclohexane, dichloromethan, chloroform, dichloroethane, hexamethylphosphoramide, dimethylimidazolidinone, N,N-dimethylformamide, N,N-dimethylacetamide, N-methylpyrrolidone, dimethyl sulfoxide, 1,3-dimethyl-3,4,5,6-tetrahydro-2-pyrimidinone, a mixed solvent thereof in any ratio, etc.) or in the absence of a solvent, in the presence or absence of a base

[alkylamine (e.g., triethylamine, diisopropylethylamine, tributylamine, etc.), aromatic amine (e.g., N,N-dimethylaniline, pyridine, 4-dimethylaminopyridine, lutidine, collidine, etc.) or a mixture of those amines, or alkali metal hydride (e.g., sodium hydride, potassium hydride, etc.)].

The step (A) in which (2R)-2-hexyloxirane is subjected to a two-carbon adding reaction with ring-opening reaction, followed by a protective reaction of a hydroxyl group to convert it to a compound represented by formula (I) may be carried out either by a single step (one pot) in which (4S)-decan-4-ol produced as an intermediate is not isolated but a hydroxyl group is subjected to a protective reaction in a reaction system, or by two steps in which the intermediate is isolated and then the hydroxyl group is subjected to a protective reaction. The conversion reaction is preferably carried out by a single step (one pot).

In the process in which the step (A) is carried out by one pot, (2R)-2-hexyloxirane is subjected to a two-carbon adding reaction with ring-opening reaction and then the resulting (4S)-decan-4-ol is subjected to a protective reaction of a hydroxyl group without isolation. Thus, (2R)-2-hexyloxirane is allowed to react with an organic metal reagent having an ethyl group in an organic solvent at −78 to 20° C. in the presence or absence of a metal catalyst, and then the protective reaction of a hydroxyl group is carried out in this reaction system. The protective reaction of a hydroxyl group is carried out at −78 to 50° C. by adding sulfonyl chloride, phosphoryl chloride or acid anhydride to the reaction mixture in the presence or absence of a base.

In a converting reaction of (2R)-2-hexyloxirane to (4S)-decan-4-ol by a two-carbon adding reaction with ring-opening reaction in the step (A), it is preferred to use tetrahydrofuran as an organic solvent. It is also preferred to use ethyl magnesium chloride as an organic metal reagent together with copper chloride which is a metal catalyst.

The compound represented by formula (I) is preferably (1S)-1-propylheptyl p-toluenesulfonate or (1S)-1-propylheptyl methanesulfonate.

In a converting reaction from (4S)-decan-4-ol to (1S)-1-propylheptyl p-toluenesulfonate which is formula (I) wherein X is p-toluenesulfonyloxy in the step (A), it is preferred that no organic solvent is used (without a solvent), p-toluenesulfonyl chloride is used as a sulfonyl chloride, and pyridine is used as a base.

In a converting reaction from (4S)-decan-4-ol to (1S)-1-propylheptyl methanesulfonate which is formula (I) wherein X is methanesulfonyloxy in the step (A), it is preferred that tetrahydrofuran is used as an organic solvent, methanesulfonyl chloride is used as a sulfonyl chloride, and triethylamine and 4-dimethylaminopyridine are used in combination as a base.

Step (B):

The conversion reaction from a compound represented by formula (I) prepared in the step (A) to (2R)-2-propyloctanamide is carried out by subjecting the compound represented by formula (I) to a one-carbon adding reaction, followed by hydrolysis.

As the one-carbon adding reaction, a cyanidation reaction is exemplified. The cyanidation reaction is known and is carried out, for example, by reacting the compound at 20 to 80° C. with a cyanidation reagent (e.g., potassium cyanide, sodium cyanide, lithium cyanide, calcium cyanide, trimethylsilyl cyanide, diethyl aluminum cyanide, t-butyl cyanide, acetone cyanohydrin, etc.) in an organic solvent (e.g., tetrahydrofuran, 2-methoxy ethyl ether, dimethoxyethane, acetonitrile, 1,4-dioxane, acetone, hexamethylphosphoramide, dimethylimidazolidinone, N,N-dimethylformamide, N,N-dimethylacetamide, N-methylpyrrolidone, dimethyl sulfoxide, 1,3-dimethyl-3,4,5,6-tetrahydro-2-pyrimidinone, a mixed solvent thereof in any ratio, etc.).

The hydrolysis reaction is also known and is carried out, for example, by reacting the compound at 0 to 50° C. with a peracid (e.g., hydrogen peroxide, t-butyl hydroperoxide, perbenzoic acid, m-chloroperbenzoic acid, an aqueous solution thereof, etc.) in an organic solvent (e.g., tetrahydrofuran, 2-methoxy ethyl ether, dimethoxyethane, acetonitrile, 1,4-dioxane, acetone, hexamethylphosphoramide, dimethylimidazolidinone, N,N-dimethylformamide, N,N-dimethylacetamide, N-methylpyrrolidone, dimethyl sulfoxide, 1,3-dimethyl-3,4,5,6-tetrahydro-2-pyrimidinone, a mixed solvent thereof in any ratio, etc.) or without a solvent.

The reaction shown by the step (B) in which the compound represented by formula (I) is subjected to a one-carbon adding reaction to give (2R)-2-propyloctanenitrile, followed by hydrolysis to convert it to (2R)-2-propylheptanamide may be carried out in one step (one pot) in which (2R)-2-propyloctanenitrile produced as an intermediate is not isolated but subjected to hydrolysis reaction in a reaction system, or may be carried out in two steps in which the intermediate is isolated and then subjected to hydrolysis reaction. The one step (one pot) method is preferred.

In the process in which the step (B) is carried out by one pot, the compound represented by formula (I) is subjected to a cyanidation reaction, and then the resulting (2R)-2-propyloctanenitrile is hydrolyzed without isolation. Thus, the compound represented by formula (I) is allowed to react with a cyanidation reagent in an organic solvent at 20 to 80° C., and then the hydrolysis reaction is carried out at the temperature of 0 to 50° C. by adding a peracid to the reaction system.

In a cyanidation reaction in the step (B) in which (1S)-1-propylheptyl p-toluenesulfonate is subjected to a one-carbon adding reaction to convert it to (2R)-2-propyloctanenitirle, it is preferred to use dimethyl sulfoxide as an organic solvent and sodium cyanide as a cyanidation reagent.

In a cyanidation reaction in the step (B) in which (1S)-1-propylheptyl methanesulfonate is subjected to a one-carbon-increasing reaction to convert it to (2R)-2-propyloctanenitrile, it is preferred to use dimethyl sulfoxide as an organic solvent and lithium cyanide as a cyanidation reagent.

In a reaction in the step (B) in which (2R)-2-propyloctanenitrile is hydrolyzed to convert it to (2R)-2-propyloctanamide, it is preferred to use dimethyl sulfoxide as an organic solvent and a 30% hydrogen peroxide solution as a peracid.

In order to obtain (2R)-2-propyloctanamide of high purity in the conversion reaction in the step (B), purification can be carried out by recrystallization, if necessary. Examples of the solvent for recrystallization include water, ethanol, methanol, n-propanol, isopropanol, n-butanol, acetonitrile, acetone, dimethoxyethane, tetrahydrofuran, ethyl acetate, isopropyl acetate, toluene, n-heptane, diethyl carbonate, t-butyl methyl ether, acetic acid, a mixed solvent of two or more of those solvents in any ratio, and the like. Preferred is a mixed solvent of water and acetonitrile.

Step (C):

The converting reaction from (2R)-2-propyloctanamide to (2R)-2-propyloctanoic acid is carried out by subjecting (2R)-2-propyloctanamide to a hydrolyzing reaction. The hydrolyzing reaction is known and carried out, for example, by reaction at 20 to 160° C. using an acid [inorganic acid (e.g., hydrochloric acid, sulfuric acid, hydrobromic acid, nitric acid, phosphoric acid, a mixture thereof, etc.), organic acid (e.g., formic acid, acetic acid, propionic acid, trifluoroacetic acid, trichloroacetic acid, methanesulfonic acid, trifluoromethanesulfonic acid, benzenesulfonic acid, p-toluenesulfonic acid, camphorsulfonic acid, oxalic acid, citric acid, a mixture thereof, etc.) or a mixture thereof, an aqueous solution thereof, etc.].

In a converting reaction of (2R)-2-propyloctanamide by hydrolysis to (2R)-2-propyloctanoic acid in the step (C), it is preferred to use a mixture of 6 mol/L hydrochloric acid and acetic acid, as an acid.

Additionally, it is also possible in the above reaction steps that, for example, in the step (A), a two-carbon adding reaction is carried out using an unsaturated organic metal reagent (e.g., vinyl magnesium chloride, vinyl magnesium bromide, ethynyl magnesium chloride, ethynyl magnesium bromide, etc.) as an organic metal reagent, the resulting (4R)-1-decen-4-ol or (4R)-1-decyn-4-ol is subjected to the reactions of the step (B) or the step (C), and the resulting (2R)-(2-propenyl)octanoic acid or (2R)-(2-propynyl)octanoic acid is reduced by the method mentioned in WO 99/58513 and WO 00/48982 to give (2R)-2-propyloctanoic acid of high purity.

Furthermore, as is apparent for the person skilled in the art, it is also possible in the present invention to produce (2S)-2-propyloctanoic acid of high purity using (2S)-2-hexyloxirane as a starting material instead of (2R)-2-hexyloxirane.

The intermediates and products prepared by the present invention can be isolated and purified by a known isolating and purifying means such as concentration, concentration in vacuo, distillation, distillation in vacuo, extraction with a solvent, crystallization, recrystallization, transfer into solvent and chromatography.

In the present invention, unless otherwise indicated, as is easily understood by the person skilled in the art, the symbol

 indicates that the substituent attached thereto is behind the sheet (i.e., α-position), the symbol  indicates that the substituent attached thereto is in front of the sheet (i.e., β-position), the symbol  indicates that it is α-position, β-position or a mixture thereof in any ratio, and the symbol / indicates that it is a mixture of α-position and β-position in any ratio.

EFFECTS OF THE INVENTION

The present invention provides a process for producing (2R)-2-propyloctanoic acid having high optical purity which is useful as a preventive and/or treating drug for neurodegenerative diseases caused by dysfunction of astrocytes starting from (2R)-2-hexyloxirane by hydrolysis via crystalline (2R)-2-propyloctanamide. The process of the present invention is a method suitable for industrial production in which (2R)-2-propyloctanoic acid can be prepared by less steps as compared with the conventional method without a dangerous reaction.

BEST MODE FOR CARRYING OUT THE INVENTION

The present invention will now be illustrated in detail by way of the following Examples although the present invention is not limited thereto. Solvents for the measurement of NMR in the following Examples are heavy chloroform in all cases.

Solvents in the passage for separation by chromatography and in parentheses for TLC are an eluting solvent or a developing solvent used therefor and the rate is ratio by volume.

EXAMPLE 1

Production of (1S)-1-propylheptyl p-toluenesulfonate:

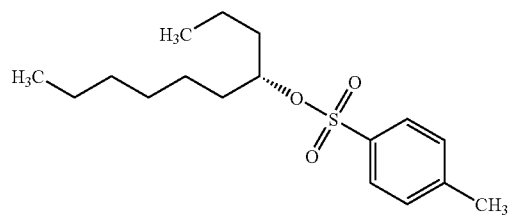

(2R)-2-Hexyloxirane (1.22 mL, 100% ee) was added dropwise to a tetrahydrofuran (2.21 mL) solution of copper chloride (15.8 mg) at −20° C. under argon atmosphere, and then a 2.11 mol/L ethyl magnesium chloride in tetrahydrofuran solution (4.55 mL) was added dropwise thereto. The reaction mixture was stirred at −20° C. for 1.5 hours, and a tetrahydrofuran solution of p-toluenesulfonyl chloride (1.83 g) was added dropwise thereto, followed by stirring for 1.5 hours. Then, the temperature was raised up to 0° C., followed by stirring for 3.5 hours. To the reaction solution were added water and pyridine, followed by stirring at 0° C. for 40 minutes, ethyl acetate was added thereto and the mixture was successively washed with 10% sulfuric acid (twice), water and brine and concentrated to give the title compound (2.27 g) having the following physical data.

TLC: Rf 0.30 (hexane:ethyl acetate=10:1); NMR: δ 0.82-0.87 (m, 6H), 1.10-1.35 (m, 10H), 1.49-1.64 (m, 4H), 2.44 (s, 3H), 4.57 (m, 1H), 7.32 (d, 2H, J=8.4 Hz), 7.79 (d, 2H, J=8.4 Hz).

EXAMPLE 2

Production of (2R)-2-propyloctanamide:

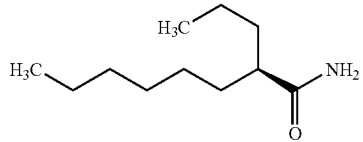

Sodium cyanide (470 mg) was added to a dimethyl sulfoxide (9.6 mL) solution of the compound prepared in Example 1 (1.5 g) under argon atmosphere, followed by stirring at 40° C. for 10 hours. The reaction mixture was cooled in a water bath, a 35% hydrogen peroxide solution (0.42 mL) was added dropwise thereto, and potassium carbonate (78.8 mg) was added thereto, followed by stirring at 40° C. 35% hydrogen peroxide solution (0.42 mL) was further added twice dropwise thereto after 1.5 hours and 6 hours after the start of the stirring at 40° C. Then, a saturated sodium sulfite solution and water were added thereto at 0° C. to precipitate crystals. The crystals were filtered and washed with water and a mixed solvent of acetonitrile and water (1:1) in this order to give the title compound (352 mg).

TLC: Rf 0.24 (hexane:ethyl acetate=1:1); NMR: δ 0.84-0.94 (m, 6H), 1.26-1.64 (m, 14H), 2.04-2.15 (m, 1H), 5.42 (bs, 1H), 5.59 (bs, 1H); Optical purity: 99.5% ee (confirmed by HPLC, from (2R)-2-hexyloxylane).

EXAMPLE 3

Production of (2R)-2-propyloctanenitrile:

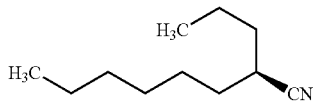

Sodium cyanide (688 mg) was added to a dimethyl sulfoxide (14 mL) solution of the compound prepared in Example 1 (2.44 g, prepared by 100% ee (4S)-decan-4-ol) under argon atmosphere, followed by stirring at 40° C. for 10 hours.

To the reaction solution was added a mixed solvent of heptane and ethyl acetate (1:9), the mixture was successively washed with water and brine and concentrated and the residue was purified by silica gel column chromatography (hexane:ethyl acetate=50:1) to give the title compound (815 mg) having the following physical data.

TLC: Rf 0.54 (hexane:ethyl acetate=10:1); NMR: δ 0.89 (t, 3H, J=6.8 Hz), 0.96 (t, 3H) J=7.0 Hz), 1.12-1.70 (m, 14H), 2.50 (m, 1H); Optical purity: 98.5% ee (confirmed by HPLC).

EXAMPLE 4

Production of (2R)-2-propyloctanamide:

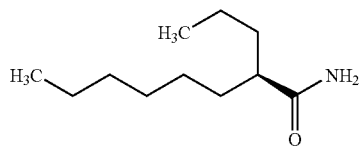

A dimethyl sulfoxide (1.95 mL) solution of the compound prepared in Example 3 (156 mg, 98.5% ee) was cooled in a water bath, a 35% hydrogen peroxide solution (0.23 mL) was added dropwise thereto, and then potassium carbonate (25.7 mg) was added thereto. The reaction mixture was stirred at 40° C. for 3 hours and a saturated aqueous solution of sodium sulfite (1 mL) and water (2 mL) were added thereto at 0° C. to precipitate crystals. The crystals were filtered and washed with heptane and water to give the title compound (172 mg).

Optical purity: 98.9% ee (confirmed by HPLC).

EXAMPLE 5

Recrystallization of (2R)-2-propyloctanamide:

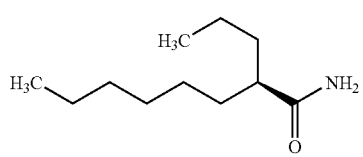

The compound prepared in Example 4 (500 mg) having optical purity of 96.0% ee was dissolved in acetonitrile (4.5 mL) and water (5.5 mL) by heating and allowed to cool and crystals precipitated were filtered. The crystals were washed with water to give the title compound (430 mg).

Optical purity: 99.5% ee (confirmed by HPLC).

EXAMPLE 6

Production of (2R)-2-propyloctanoic acid

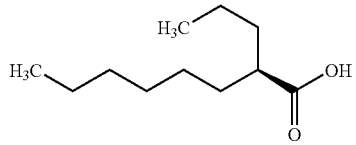

Acetic acid (0.35 mL) and 6 mol/L hydrochloric acid (0.35 mL) were added to the compound prepared in Example 2 or 5 (70 mg, 99.5% ee), followed by stirring at 130° C. for 10 hours. The reaction mixture was allowed to cool, heptane was added thereto and the mixture was washed with a brine and concentrated. The residue was purified by silica gel column chromatography (hexane:ethyl acetate=2:1) to give the title compound (52.4 mg) having the following physical data.

TLC: Rf 0.54 (hexane:ethyl acetate=7:3); NMR: δ 0.86-0.93 (m, 6H), 1.25-1.50(m, 12H), 1.57-1.67 (m, 2H), 2.36 (m, 1H); Optical purity: 99.2% ee (derived to phenacyl ester, followed by confirmation of optical purity by HPLC).

EXAMPLE 7

Production of (2S)-2-propyloctanoic acid

The same operations as in Example 1→Example 2→Example 6 were carried out using (2S)-2-hexyloxirane instead of (2R)-2-hexyloxirane to give the compound of the present invention having the following physical data.

TLC: Rf 0.54 (hexane:ethyl acetate=7:3); NMR: δ 0.86-0.93 (m, 6H), 1.25-1.50 (m, 12H), 1.57-1.67 (m, 2H), 2.36 (m, 1H); Optical rotation: $[\alpha]_D$+5.19 (c=2.70, chloroform).

INDUSTRIAL APPLICABILITY

The present invention provides a process for producing (2R)-2-propyloctanoic acid in high optical purity which is useful as a preventive and/or treating drug for neurodegenerative diseases caused by dysfunction of astrocytes starting from (2R)-2-hexyloxirane by hydrolysis via crystalline (2R)-2-propyloctanamide. The process of the present invention is a method suitable for industrial production in which (2R)-2-propyloctanoic acid is able to be prepared by less steps as compared with the conventional method without a dangerous reaction.

The invention claimed is:

1. A process for producing (2R)-2-propyloctanoic acid, which comprises:
    subjecting (2R)-2-hexyloxirane to a two-carbon adding reaction with ring-opening reaction, followed by a reaction to protect the hydroxyl group with a removable protective group by reacting the hydroxyl group with a sulfonyl chloride, a phosphoryl chloride or an acid anhydride to obtain a compound represented by formula (I):

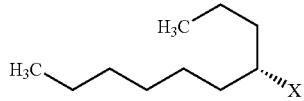 (I)

wherein X represents a hydroxyl group which is protected by a removable protective group, and then
subjecting the compound to a one-carbon adding reaction to obtain (2R)-2-propyloctanamide, followed by recrystallization and hydrolysis.

2. A process for producing (2R)-2-propyloctanoic acid, which comprises hydrolyzing isolated (2R)-2-propyloctanamide.

3. A process for producing (2R)-2-propyloctanamide, which comprises subjecting a compound represented by formula (I):

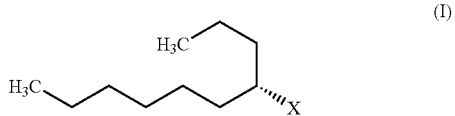 (I)

wherein X represents a hydroxyl group which is protected by a removable protective group,
to a one-carbon adding reaction.

* * * * *